US012672832B2

(12) United States Patent
Lee et al.

(10) Patent No.: US 12,672,832 B2
(45) Date of Patent: Jul. 7, 2026

(54) METHODS AND SYSTEMS FOR GENERATING A DIAGNOSIS VIA A DIGITAL HEALTH APPLICATION

(71) Applicant: GPS Health LLC, New York, NY (US)

(72) Inventors: Thomas Lee, New York, NY (US); Alphan Kirayoglu, New York, NY (US); Alexander Fabry, Brooklyn, NY (US); Brian Shi, New York, NY (US)

(*) Notice: Subject to any disclaimer, the term of this patent is extended or adjusted under 35 U.S.C. 154(b) by 0 days.

(21) Appl. No.: 16/935,614

(22) Filed: Jul. 22, 2020

(65) Prior Publication Data

US 2021/0022688 A1     Jan. 28, 2021

Related U.S. Application Data

(60) Provisional application No. 62/878,979, filed on Jul. 26, 2019.

(51) Int. Cl.
*A61B 5/00*      (2006.01)
*G06F 3/0482*    (2013.01)
          (Continued)

(52) U.S. Cl.
CPC .......... *A61B 5/7475* (2013.01); *A61B 5/0022* (2013.01); *A61B 5/7264* (2013.01);
          (Continued)

(58) Field of Classification Search
USPC ........................................................ 715/810
See application file for complete search history.

(56) References Cited

U.S. PATENT DOCUMENTS 6,090,044 A * 7/2000 Bishop ................ A61B 5/1071
                                                            128/920
7,780,595 B2 * 8/2010 Iliff ........................ G16H 50/20
                                                            600/300
(Continued)

FOREIGN PATENT DOCUMENTS

KR     20170098414 A     8/2017
WO      2021021549 A1    2/2021

OTHER PUBLICATIONS

International Search Report and Written Opinion mailed Nov. 11, 2020, in international patent application No. PCT/US2020/043227, 9 pages.
(Continued)

*Primary Examiner* — William L Bashore
(74) *Attorney, Agent, or Firm* — Blueshift IP, LLC; Cynthia M. Gilbert

(57)          ABSTRACT

A method for generating a diagnosis via a digital health application includes receiving, by a digital health application, a request for a diagnosis. A digital health application selects a plurality of questions based on the initial complaint, an order of presenting each of the plurality of questions, the order associated with the plurality of questions. The digital health application displays, to a user of the digital health application, in the associated order, each of the plurality of questions. The digital health application receives user input responsive to the questions. The digital health application determines a diagnosis and modifies a user interface to display an identification of the determined diagnosis. The digital health application requests an indication of whether the user of the digital health application accepts the diagnosis. The digital health application requests an indication of whether to establish a consultation with a medical professional to discuss the diagnosis.

19 Claims, 10 Drawing Sheets

(51) Int. Cl.

| | |
|---|---|
| *G16H 10/20* | (2018.01) |
| *G16H 10/60* | (2018.01) |
| *G16H 40/20* | (2018.01) |
| *G16H 40/67* | (2018.01) |
| *G16H 50/20* | (2018.01) |
| *G16H 50/70* | (2018.01) |
| *G16H 80/00* | (2018.01) |

(52) U.S. Cl.

CPC .......... *A61B 5/7435* (2013.01); *G06F 3/0482* (2013.01); *G16H 10/20* (2018.01); *G16H 10/60* (2018.01); *G16H 40/20* (2018.01); *G16H 40/67* (2018.01); *G16H 50/20* (2018.01); *G16H 50/70* (2018.01); *G16H 80/00* (2018.01)

(56) References Cited

U.S. PATENT DOCUMENTS

| | | | |
|---|---|---|---|
| 2006/0129433 A1* | 6/2006 | Koneru | G16H 10/60 600/300 |
| 2006/0135859 A1* | 6/2006 | Iliff | G16H 40/63 600/300 |
| 2007/0255599 A1* | 11/2007 | Henry | G16H 10/60 705/3 |
| 2009/0018862 A1 | 1/2009 | Sanger | |
| 2012/0035962 A1 | 2/2012 | Iliff | |
| 2012/0078837 A1 | 3/2012 | Bagchi | |
| 2012/0101846 A1* | 4/2012 | Gotthardt | G16H 40/63 705/3 |
| 2014/0019149 A1* | 1/2014 | Yu | G16H 40/20 705/2 |
| 2014/0088985 A1* | 3/2014 | Grant | G16H 40/67 705/2 |
| 2014/0201627 A1* | 7/2014 | Freeman | G06F 3/0485 715/771 |
| 2015/0100521 A1 | 4/2015 | Kozloski | |
| 2015/0379232 A1 | 12/2015 | Mainwaring | |
| 2016/0042133 A1* | 2/2016 | Sidel | G16H 50/20 705/51 |
| 2016/0098542 A1* | 4/2016 | Costantini | G16H 10/60 705/3 |
| 2017/0344711 A1 | 11/2017 | Liu | |
| 2018/0068083 A1* | 3/2018 | Cohen | G16B 50/30 |
| 2018/0110475 A1* | 4/2018 | Shaya | G16H 10/60 |
| 2018/0246890 A1 | 8/2018 | Brown | |
| 2019/0087902 A1* | 3/2019 | Dawkins | G06Q 40/08 |
| 2019/0295719 A1* | 9/2019 | Van De Steen | G06Q 50/24 |
| 2019/0311814 A1* | 10/2019 | Kannan | G16H 50/50 |

OTHER PUBLICATIONS

Extended European Search Report issued in App. No. EP20846503, dated Jul. 14, 2023, 10 pages.

* cited by examiner

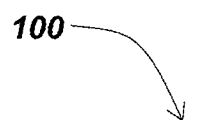
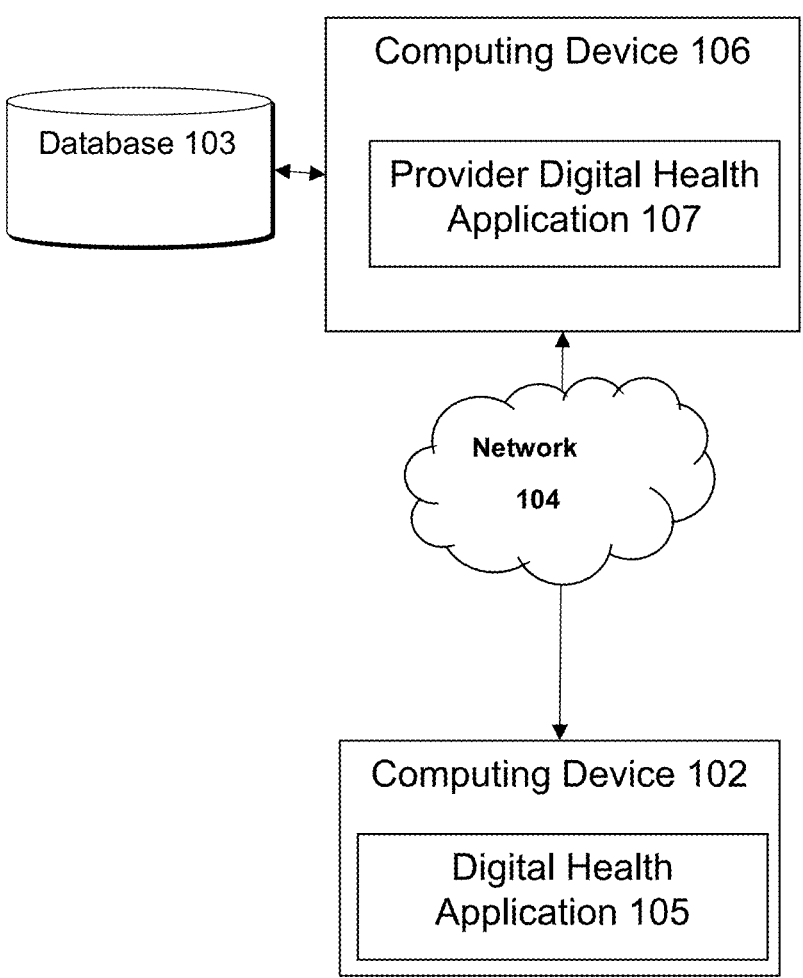
*Fig. 1A*

100

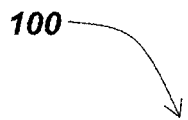

100

How long have you had nasal congestion?

- ◯ < 1 week
- ◉ 1-2 weeks
- ◯ 3-4 weeks
- ◯ 4-6 weeks
- ◯ > 6 weeks

Have you also had any of the following associated symptoms?

- ☐ cough or other cold symptoms
- ☒ nasal itching
- ☐ itchy/watery eyes
- ☐ fever >101
- ☐ sinus pain/pressure
- ☒ yellow/green nasal discharge
- ☐ congestion consistently on just one side
- ☐ None of the above

Which describe the pattern of your symptoms?

- ☐ consistent since starting
- ☒ started improving then got worse again
- ☐ intermittent with a clear trigger
- ☐ intermittent but no clear trigger
- ☐ worse during the work week, improved when away from work
- ☐ seasonal
- ☐ year-round/persistent
- ☐ None of the above

To confirm, do you have any of the following medical conditions?

- ☐ acid reflux / heartburn
- ☐ asthma
- ☐ eczema
- ☐ personal history of sinus allergies
- ☐ deviated septum
- ☒ history of recurrent sinus infections
- ☐ previous sinus surgery
- ☐ None of the above

Did any of the following precede your symptoms?

- ☒ regular use of over the counter nasal decongestant spray
- ☐ acquired a new pet
- ☐ a new prescription medication
- ☐ pregnancy
- ☐ moved my home or workplace
- ☐ started to use a CPAP machine
- ☐ cocaine use
- ☐ None of the above

Some symptoms may require more attention. To confirm, do you have any of the following?

- ☒ Persistent or recurrent nasal obstruction (complete blockage) on 1 side only
- ☐ Clear fluid leaking from my nose that seems thinner than mucous, especially when leaning forward
- ☐ Sinus infection symptoms for more than 12 weeks
- ☐ At least 4 episodes of diagnosed sinus infection in the past year
- ☐ Eye pain and eyelid swelling
- ☐ None of the above

*Fig. 1C*

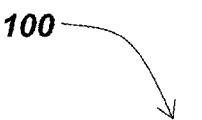
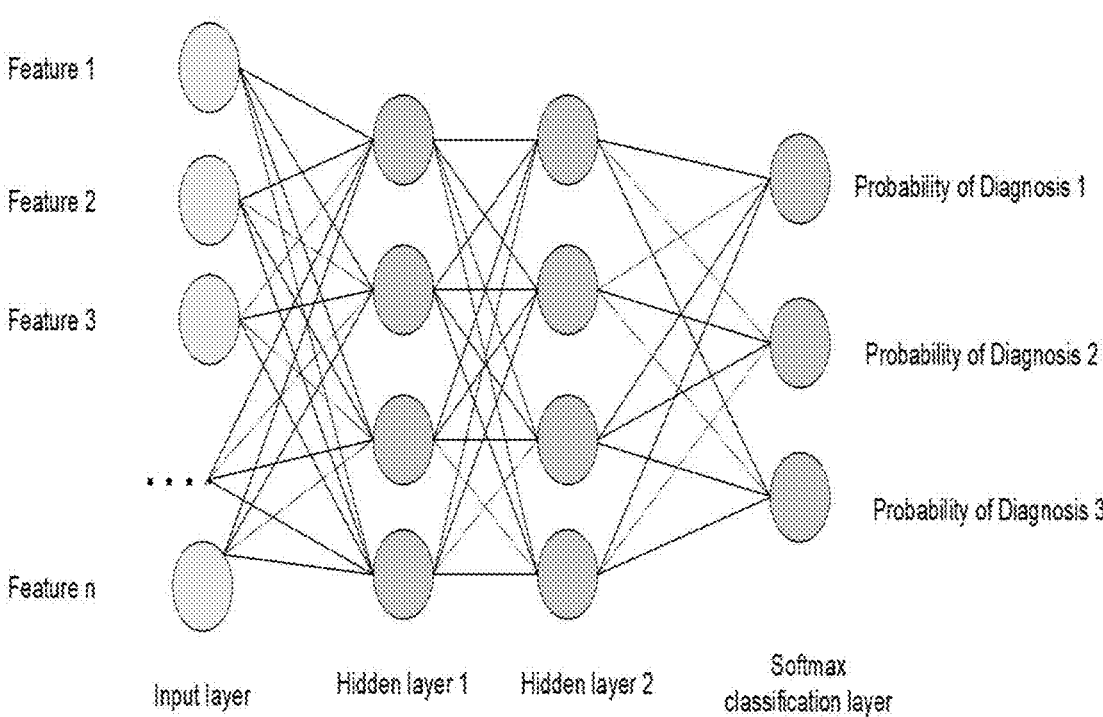
*Fig. 1D*

*100*

*200*

Receiving, by a Digital Health Application Executing on a
Computing Device, a Request for a Diagnosis Including an Initial
Complaint
202

Selecting, by the Digital Health Application, a Plurality of
Questions from a Database Based on the Initial Complaint, an
Order of Presenting Each of the Plurality of Questions, the Order
Associated with the Plurality of Questions
204

Displaying, to a User of the Digital Health Application, in the
Associated Order, Each of the Plurality of Questions
206

Receiving, by the Digital Health Application, User Input
Responsive to Each of the Plurality of Questions
208

Determining, by the Digital Health Application, a Diagnosis Based
Upon the Received User Input
210

Modifying, by the Digital Health Application, a User Interface of
the Digital Health Application to Display an Identification of the
Determined Diagnosis
212

Requesting, by the Digital Health Application, an Indication of
Whether the User of the Digital Health Application Accepts the
Determined Diagnosis
214

Requesting, by the Digital Health Application, an Indication of
Whether to Establish, for the User of the Digital Health
Application, a Consultation with a Medical Professional to Discuss
the Determined Diagnosis
216

*Fig. 2*

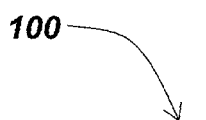
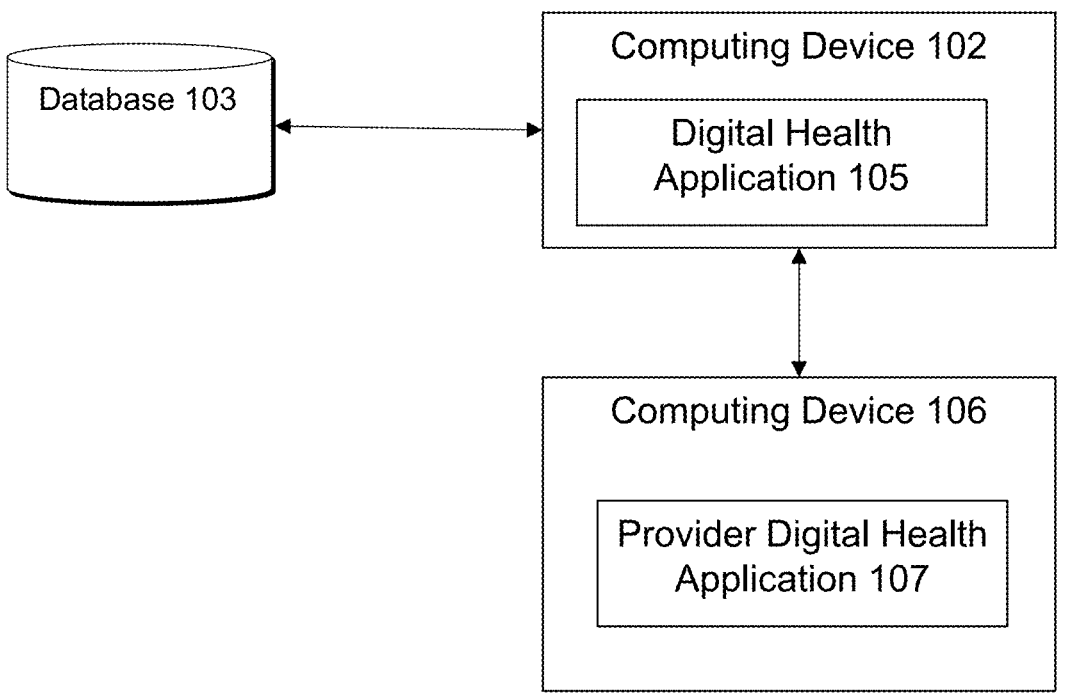
*Fig. 3*

METHODS AND SYSTEMS FOR GENERATING A DIAGNOSIS VIA A DIGITAL HEALTH APPLICATION

CROSS-REFERENCE TO RELATED APPLICATIONS

This application claims priority from U.S. Provisional Patent Application No. 62/878,979, filed on Jul. 26, 2019, entitled, "Methods and Systems for Generating a Diagnosis via a Digital Health Application," which is hereby incorporated by reference.

BACKGROUND

The disclosure relates to generating medical diagnoses. More particularly, the methods and systems described herein relate to functionality for generating diagnoses via digital health applications.

There are publishers of news and information pertaining to human health and well-being, including information pertaining to medicine, and such publishers provide suggestions regarding topics of interest to users based on collections of symptoms. However, this published information does not typically provide actionable data for the users.

There are conventional systems for receiving urgent care in which a patient typically provides one or more symptoms to a medical professional, waits for some period of time (varying between a few minutes and a few hours depending on the urgency and availability of the medical professional) to receive advice regarding whether to schedule an in-person appointment, acquire and use over-the-counter or at-home treatments, or to have the medical professional send a prescription to a nearby pharmacy for the patient's use. However, such a system is typically highly dependent on availability and cannot always provide immediate, on-demand support. Furthermore, such a system typically provides only assistance with acute issues and does not address a patient's on-going needs. Additionally, such systems typically involve an inefficient back-and-forth process between a patient and a clinician. As such, the patient is not typically receiving truly excellent medical care and the care provided is typically of a highly variable quality.

Therefore, there is a need for a virtual primary care practice that provides efficient, actionable data to patients.

BRIEF SUMMARY

In one aspect, a method for generating a diagnosis via a digital health application includes receiving, by a digital health application executing on a computing device, a request for a diagnosis including an initial complaint. The method includes selecting, by the digital health application, a plurality of questions from a database based on the initial complaint, an order of presenting each of the plurality of questions, the order associated with the plurality of questions. The method includes displaying, by the digital health application, to a user of the digital health application, in the associated order, each of the plurality of questions. The method includes receiving, by the digital health application, user input responsive to each of the plurality of questions. The method includes determining, by the digital health application, a diagnosis based upon the received user input. The method includes modifying, by the digital health application, a user interface of the digital health application to display an identification of the determined diagnosis. The method includes requesting, by the digital health application, an indication of whether the user of the digital health application accepts the determined diagnosis. The method includes requesting, by the digital health application, an indication of whether to establish, for the user of the digital health application, a consultation with a medical professional to discuss the determined diagnosis.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIG. 1A is a block diagram depicting an embodiment of a system for generating a diagnosis via a digital health application;

FIG. 1C is a screen shot depicting an example of a set of questions presented to a user by a digital health application;

FIG. 1D is a flow diagram depicting one embodiment of a prediction model provided as a neural network;

FIG. 2 is a flow diagram depicting an embodiment of a method for generating a diagnosis via a digital health application;

FIG. 3 is a block diagram depicting an embodiment of a system for generating a diagnosis via a digital health application.

DETAILED DESCRIPTION

Figure 1B:
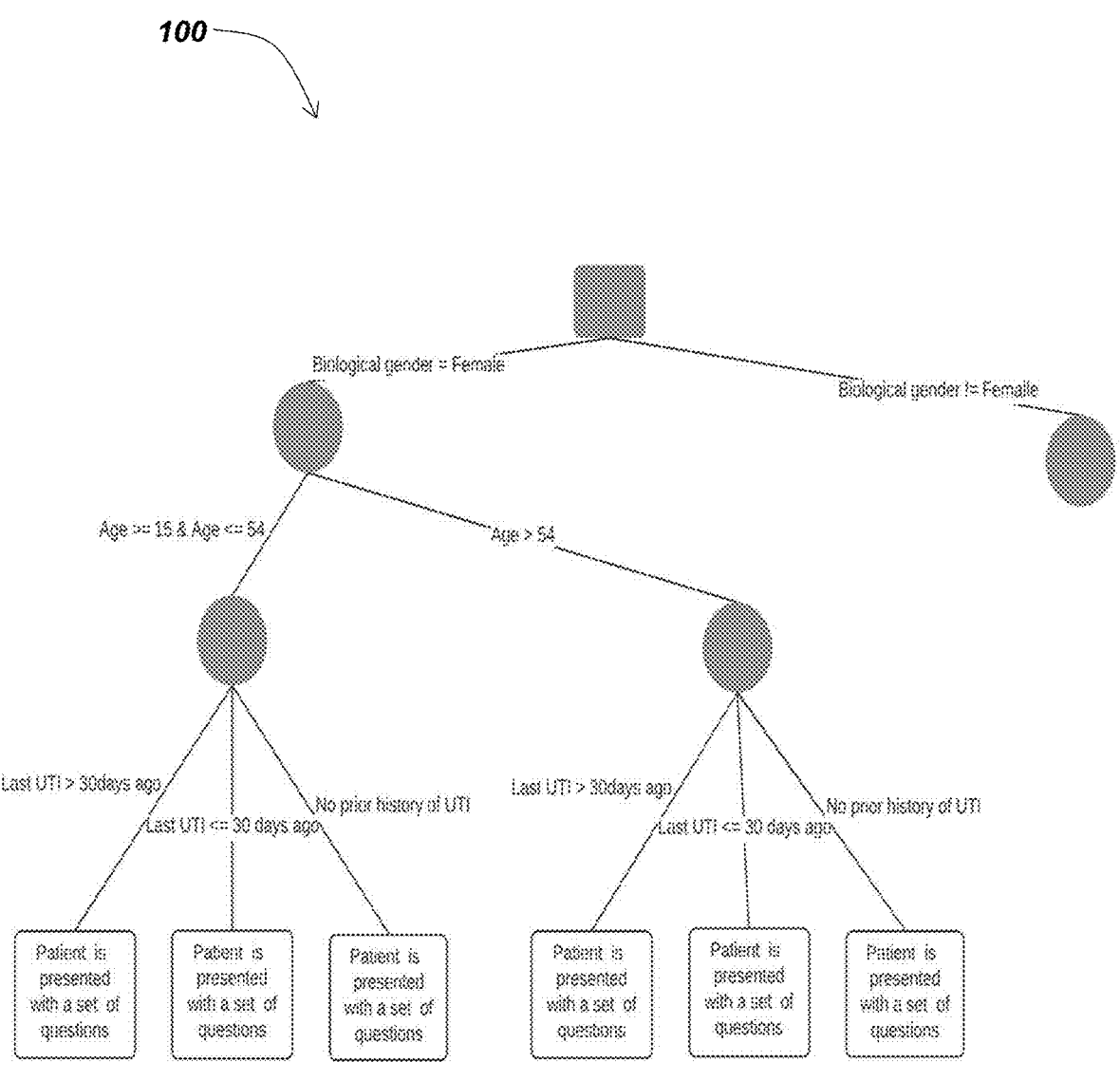
FIG. 1B is a flow diagram depicting an embodiment of a decision tree used in selecting questions to present to users when generating a diagnosis via a digital health application.

The present disclosure relates to methods and systems for generating a diagnosis via a digital health application. In one embodiment, the methods and systems described herein provide functionality for generating medical diagnoses (for example, and without limitation, predictively or through machine learning), and to enable a patient to accept the generated diagnosis and/or to initiate a consultation with a medical professional.

Referring now to FIG. 1, a block diagram depicts one embodiment of a system 100 for generating a diagnosis via a digital health application. The system 100 includes a computing device 102, a database 103, a network 104, a computing device 106, digital health applications 105a-n (referred to generally as a digital health application 105), and a provider digital health application 107.

The computing device 102 may be provided as a computing device 402, described in greater detail below in connection with FIGS. 4A-4C. The computing device 102 may execute a web browser or mobile phone application with which the computing device 102 may access the digital health application 105 and receive data for display to a user of the computing device 102. The computing device 102 may execute a client-side application that provides a user interface with which a user of the computing device 102 may interact with the remotely executing digital health application 105. The computing device 102 may execute the digital health application 105 locally. Alternatively, the computing device 102 may access a digital health application 105 that executes on the computing device 106.

The computing device 106 may be referred to as a server 106. The computing device 106 may be provided as a computing device 406, described in greater detail below in connection with FIGS. 4A-4C. The computing device 106 may host the digital health application 105. The computing device 106 may be in communication with a digital health application 105 executing on a different computing device 1*o*6*b* (not shown). The computing device 106 may provide the digital health application 105 with access to data for use in generating medical diagnoses (e.g., access to electronic medical records systems, data associated with medical professionals, scheduling data, and diagnostics information). The computing device 1*o*6 may execute the provider digital health application 107.

The database 103 may store one or more questions for use in reaching a medical diagnosis. The database 103 may be an ODBC-compliant database. For example, the database 103 may be provided as an ORACLE database, manufactured by Oracle Corporation of Redwood Shores, CA. In other embodiments, the database 103 can be a Microsoft ACCESS database or a Microsoft SQL server database, manufactured by Microsoft Corporation of Redmond, WA. In other embodiments, the database 103 can be a SQLite database distributed by Hwaci of Charlotte, NC, or a PostgreSQL database distributed by The PostgreSQL Global Development Group. In still other embodiments, the database 103 may be a custom-designed database based on an open source database, such as the MYSQL family of freely available database products distributed by MySQL AB Corporation of Uppsala, Sweden. In other embodiments, examples of databases include, without limitation, structured storage (e.g., NoSQL-type databases and BigTable databases), HBase databases distributed by The Apache Software Foundation of Forest Hill, MD, MongoDB databases distributed by 10Gen, Inc., of New York, NY, and Cassandra databases distributed by The Apache Software Foundation of Forest Hill, MD. In further embodiments, the database 103 may be any form or type of database.

The digital health application 105 may be a software module. The digital health application 105 may be hardware module. The digital health application 105 may have access to patient electronic medical records. The digital health application 105 may have access to functionality for scheduling consultations or appointments between patients and medical professionals. The digital health application 105 may have functionality for generating and transmitting prescriptions and other medical orders to fulfillment centers. The digital health application 105 may have functionality for providing users with information regarding wellness management and disease management. The digital health application 105 may access predictive model parameters. The digital health application 105 may access a patient health history.

The digital health application 105 may execute on an application server 106. The digital health application 105 may execute on a client device 102 (such as a user's computer or mobile device). The digital health application 105 may be in communication with the provider digital health application 107. The digital health application 105 may have access to the database 103, directly (as shown in FIG. 3) or indirectly (as shown in FIG. 1A).

The provider digital health application 107 may be a software module. The provider digital health application 107 may be hardware module. The provider digital health application 107 may provide access to at least one electronic medical record. The provider digital health application 107 may provide access to a provider collaboration tool.

The digital health application 105 may execute in a patient-facing mode, providing patient-facing clinical interaction and engagement interface, or in a provider-facing mode, providing access to an electronic medical record and provider collaboration tool, and including content management functionality to create a corpus of questions that may be displayed to the patient. In an embodiment in which the digital health application 105 executes in a provider-facing mode, the digital health application 105 replaces the provider digital health application 107.

Although for ease of discussion, only one computing device 102, database 103, computing device 106, digital health application 105, and provider digital health application 107 are shown in FIG. 1A, those of ordinary skill in the art will understand that multiple of any and/or each of these devices may be provided.

Referring now to FIG. 2, a flow diagram depicts one embodiment of a method 200 for generating a diagnosis via a digital health application. In brief overview, the method 200 includes receiving, by a digital health application executing on a computing device, a request for a diagnosis including an initial complaint (202). The method 200 includes selecting, by the digital health application, a plurality of questions from a database based on the initial complaint, an order of presenting each of the plurality of questions, the order associated with the plurality of questions (204). The method 200 includes displaying, by the digital health application, to a user of the digital health application, in the associated order, each of the plurality of questions (206). The method 200 includes receiving, by the digital health application, user input responsive to each of the plurality of questions (208). The method 200 includes determining, by the digital health application, a diagnosis based upon the received user input (210). The method 200 includes modifying, by the digital health application, a user interface of the digital health application to display an identification of the determined diagnosis (212). The method 200 includes requesting, by the digital health application, an indication of whether the user of the digital health application accepts the determined diagnosis (214) or requests that the digital health application establish, for the user of the digital health application, a consultation with a medical professional to discuss the determined diagnosis or have a medical professional review the patient file and determined diagnosis (216).

In some embodiments, for each type of diagnosis the digital health 105 could reach, the digital health application 105 has received, or has access to, a set of questions and an order in which to ask the questions. The order may be based on input from medical professionals. The order may be based on patient age. The order may be based on patient gender. The order may be based on seasonality. Diagnostic monographs, or other clinical decision-making frameworks, which may determine the order of questions, may be altered based on the clinical decisions and outcomes generated by the system 100 over a period of time. A diagnostic monograph may be a set of questions and answers for a given patient group (may defined by age, gender and comorbidities) that will accurately collect the most pertinent (historical) elements to differentiate between the most common and most dangerous diagnoses on a differential diagnosis for a given "chief complaint" or concern reported by the patient.

In some embodiments, the order of the questions is static. In other embodiments, the order of the questions is static but there are variations on the orders assigned to a set of questions based on data associated with users (e.g., age and gender). In further embodiments, the digital health application 105 receives an initial set of questions and an initial order in which to ask the questions but evolves (e.g., modifies) the set of questions and the order over time. In one of these embodiments, a modification to the order may be triggered based on data associated with the user. For example, the digital health application 105 may identify information in a user health record and/or demographic history that may affect care (e.g., an indication of breast cancer). In another of these embodiments, the digital health application 105 may access a decision tree to determine whether to modify an initial order of the questions. In still another of these embodiments, the modification is based on an application of machine learning algorithms to the process (for example, by determining whether a patient or medical professional confirmed a medical diagnosis as an accurate diagnosis and having a machine learning algorithm determine that the order of questions asked and the questions themselves contributed to the accuracy of the diagnosis and applying that determination in generating subsequent questions). The digital health application may also apply machine learning algorithms to predict the diagnosis, as described in further detail below. The digital health application may also apply machine learning algorithms to use natural language processing on unstructured patient documents available from other care providers to identify previous conditions, treatment history, allergies, procedures, and other data.

Referring now to FIG. 1B, FIG. 1B is a flow diagram depicting an embodiment of a decision tree used in selecting questions to present to users when generating a diagnosis via a digital health application. As shown in FIG. 1B, the sets of questions and their associated orders may be represented as a decision tree, in which each leaf of the decision tree may represent binary or multivariate options; each leaf node may have a role in determining a patient's medical diagnosis. Using the decision tree, the digital health application 105 may query various data sources (including, without limitation, a patient's medical history). By way of example, a patient's biological gender and age group can be represented as individual nodes on the decision tree; a patient's medical history (including for example, chronic conditions and recent diagnoses) may be represented as nodes in the decision tree. Acuteness and duration of the patient's complaint may be also expressed as nodes in the decision tree. Based on patient's existing data in the database and input in the digital health application 105, questions from a subtree of the decision tree may be selected and presented to a user.

Referring now to FIG. 2, in greater detail and in connection with FIGS. 1A-1E, the method 200 includes receiving, by a digital health application executing on a computing device, a request for a diagnosis including an initial complaint (202). The system 100 may provide a user interface with which the user may transmit the request for the diagnosis and the initial complaint.

The method 200 includes selecting, by the digital health application, a plurality of questions from a database based on the initial complaint, an order of presenting each of the plurality of questions, the order associated with the plurality of questions (204). The digital health application 105 may access a table or other data structure stored, for example, in a database. The digital health application 105 may identify a key word in the initial complaint and use the key word to perform a key word search of a database 103 to identify the plurality of questions. The digital health application 105 may access a database to retrieve data based on patient inputs (e.g., responses to each of the questions as they are received or to data provided in the initial complaint). The digital health application 105 may access a database to retrieve data based on data associated with the patient, including, without limitation, historical factors and demographic factors. For two patients with the same initial complaint, the digital health application 105 may retrieve a first plurality of questions from the database for the first patient while retrieving a second plurality of questions for a second patient. By way of example, besides age and gender, medical comorbidities such as history of heart disease, diabetes, high cholesterol and history of smoking may alter the set of questions presented to the patient as these comorbidities would determine if the patient is high cardiac risk vs low cardiac risk. As another example, besides age and gender, medical history of the patient may be used to determine if there is a prior history of migraines and also determine if there is a previous history of acute headaches; if migraines are present as a comorbidity in their medical history, a patient may be presented with a different set of questions vs a patient with no history of migraines.

The digital health application 105 may store, in one or more database tables (including, e.g., both relational and non-relational databases), sets of questions (and their order), the sets of answers for each question and their order and the type of potential response (e.g., multiple choice vs. single choice vs. free-text). By way of example, the digital health application 105 may store a unique template for—as an example—female patients, age 15-54 who did not have a UTI in the last 30 days. The digital health application 105 may store in a table a mapping of relevant questions associated with a unique template and store an associated ranking (e.g., the order of the questions to be presented). As an example, and without limitation, in one embodiment, the basic schema of such a table may be: form_questions table: templated_id, question_id, rank. Similarly, in a separate table, the digital health application 105 may store a mapping of relevant answer options to a unique question; this table may also store the rank (order of the answer) when they are presented in the UI. As an example, the basic schema of such a table may be: question_answers table: question_id, answer_id, rank. A corpus of questions and answers may be stored in separate database tables. As examples, a basic schema of a questions table may be: question_id: question_text: Do you also have any of the following?; question_type: multi-choice; and a basic schema of the corresponding answers table may be answer_id: answer_text: fever >100 F.

The digital health application 105 may initiate a process of displaying, and receiving responses to, a sequence of questions from the plurality of questions.

The method 200 includes displaying, by the digital health application, to a user of the digital health application, in the associated order, each of the plurality of questions (206). Referring to FIG. 1C, a screen shot shows an example of a set of questions presented to a user.

Referring back to FIG. 2, the method 200 includes receiving, by the digital health application, user input responsive to each of the plurality of questions (208). The user input may include a text-based response via a user interface. The user input may include a photograph submitted via a user interface. The user input may include a video (e.g., an audiovisual file) submitted via a user interface. When a user submits a video file, the video may provide information related to the question (e.g., a video showing a wound or how a limb moves or does not move given an injury, etc.). The submitted video may also, or instead, provide a response to one or more questions. The user may also provide video that includes a video of the user providing the initial complaint. The system 100 may include functionality for applying one or more techniques for text capture or other functionality for converting one or more audio segments of an audiovisual file to extract information from the video for use by the digital health application 105. In some embodiments, the video may be captured outside of the digital health application 105 (e.g., by a user's camera or device including camera functionality separate from the system 100) or may be captured as part of an interaction via the user interface of the digital health application 105 (e.g., a user interface, not shown, allowing the user to submit audiovisual files in response to questions).

Upon receiving user input responsive to a first question in the plurality of questions, the digital health application 105 may modify the display of a user interface to display a second of the plurality of questions, the second of the plurality of questions chosen based upon the associated order. In some embodiments, the digital health application 105 may modify the order associated with the plurality of questions based upon an analysis of received user input; the digital health application 105 may, therefore, select and display a second of the plurality of questions based upon the modified order instead of the order initially associated with the plurality of questions.

As the digital health application 105 receives input responsive to each of the plurality of questions, the digital health application 105 may begin generating a diagnosis—for example, the digital health application 105 may generate an enumeration of possible diagnoses when a first response is received and then filter out a subset of the enumerated possible diagnoses after a second response is received. Depending on the improvement in probability with each additional question answered, the digital health application 105 may continue asking questions or the digital health application 105 may determine that it has obtained adequate info to make an accurate diagnosis.

The digital health application 105 may integrate data based upon analyses of individual user data, data associated with a plurality of users in a database, and data retrieved from other publicly available databases.

The method 200 includes determining, by the digital health application, a diagnosis based upon the received user input (210). The digital health application 105 may determine the diagnosis by analyzing received user inputs. The digital health application 105 may execute natural language processing techniques to free-text answers provided by patients to generate data that is in a format the digital health application 105 can analyze. The digital health application 105 may apply techniques to identify one or more features of a free-text input or of a photo, a video, a file in a portable document format, or other additional material provided with the user input and use the identified feature as a feature in a model applied to determine the diagnosis, as described in greater detail below. The digital health application 105 may extract data from the received user input and generate features to provide as input to a model applied in determining a diagnosis. For example, user inputs and demographics can be translated into dummy variables such as the gender=1 for female and 0 for male, fever=1 when the patient say fever >104, and 0 otherwise. As another example, the digital health application 105 may combine one or more user inputs to generate a feature to provide as input to a model applied in determining a diagnosis. The digital health application 105 may determine the diagnosis by analyzing data associated with the patient; for example, such associated data may include the user's past medical information and population data from past encounters of other patients and/or publicly available population-level data.

The digital health application 105 may generate a list of diagnoses and assigned probabilities by applying a model based on the patient's initial complaint. The digital health application 105 may apply a linear model to determine a level of probability of the diagnosis. The digital health application 105 may apply a neural network model to determine a level of probability of the diagnosis. The model may be in the form of a linear multinomial response model or a neural network structure with a multi-class classification outer layer. The coefficients (in a linear multinomial response model) or the hyperparameters (in a neural network structure) of the model may be retrieved from a database. The model may use information from a patient's demographic profile, medical history and the received responses to the prompted questions for feature generation for the model. The digital health application 105 may determine the diagnosis through the use of coefficients applied to one or more variables and patient medical histories, in addition to received user input; the digital health application 105 may convert the received user input into the one or more variables. Model coefficients, patient medical histories, and publicly available data may be stored in a database 103; as will be understood by those of ordinary skill in the art, the model coefficients, patient medical histories, and publicly available data may be stored in different data structures (such as tables) in the database 103 or they may be stored in separate databases. The digital health application 105 may couple the coefficients aligned with stored parameters with the collected answers (the received user input); the digital health application 105 may then incorporate the sub-information (e.g., demographics) and generate probabilities of different diagnoses (and may, without limitation, rank the probabilities and select a first diagnosis with a higher probability than a second diagnosis).

The models applied by the digital health application 105 may take in as initial input (and/or be trained based upon) logic and clinical decision-making framework data created and adapted based on founder expertise, refined by feedback data and outcomes. The models applied by the digital health application 105 may be take in as initial input (and/or be trained based upon) clinical insights and expertise used to adapt framework and adjust clinical data inputs. The models applied by the digital health application 105 may be take in as initial input (and/or be trained based upon) clinical data inputs collected from patients on the mobile device and other data sources. The models applied by the digital health application 105 may be take in as initial input (and/or be trained based upon) clinical decisions and outcomes captured over time.

The following is an illustrative example of an embodiment of a linear multinomial response model that the digital health application 105 may apply in determining a diagnosis:

$$Y = \beta_0 + \beta_1 \text{ gender} + \beta_2 \text{ age}_{group} + \beta_3 \text{ last}_{UTI} + \vec{\beta} \vec{X}$$

where, gender=1 if female; gender=0 otherwise age_group=1 if 15<=age <55; age_group=0 otherwise last_UTI=1 if the last UTI >30 days ago; last_UTI=0 otherwise.

X represents a vector of other features engineered from patient's answers input in application 105 and patient's medical history. It may include features related to a patient's symptoms and (ex fever, vomiting, back-pain, vaginal irritation) and their duration. It may also include the symptoms for previous occurrences of the same complaint by the patient. Output of the model will be a vector of log likelihoods assigned to different diagnoses. For example, $$
Y = [ \\
\quad \text{Log Likelihood}_{UTI}, \\
\quad \text{Log Likelihood}_{Pyelonephristis}, \\
\quad \text{Log Likelihood}_{Yeast\ infections}, \\
\quad \text{Log Likelihood}_{Trichomonas}, \\
\quad \text{Log Likelihood}_{Chlamydia}, \\
\quad \text{Log Likelihood}_{Other} \\
]
$$

Then application 105 may display a subset of these diagnoses for the patient to accept one or choose to interact with a medical professional, as described in greater detail below. Models can be modified and re-trained based on guidance from the clinical team and as more patient data is collected through the application. New features may be added, features may be engineered differently or the coefficients of the model can be estimated using different underlying training datasets.

Referring now to FIG. 1D, a flow diagram depicts one embodiment of a prediction model provided as a neural network. As shown in FIG. 1D, the topology of the neural network may include an input layer, one or more hidden layers, and a classification output layer. Each of the layers may include one or more nodes. In some embodiments, every node in one layer is connected to every other node in the next layer. A node may pass the weighted sum of its inputs through a non-linear activation function and pass its results to one or more nodes in the next layer as inputs. Models can be modified and re-trained based on guidance from the clinical team and as more patient data is collected through the digital health application 105. The topology of the model may be modified or the hyperparameters of the model can be estimated using different underlying training datasets.

Referring back to FIG. 2, The digital health application 105 may determine the diagnosis by analyzing the received user input and medical history data associated with the user (e.g., the digital health application 105 may access one or more portions of an electronic medical record of the user and use that medical history in reaching a diagnosis). The medical history data may include longitudinal medical history data; therefore, the digital health application 105 may determine the diagnosis based upon the received user input and upon longitudinal data associated with the user. The digital health application 105 may determine the diagnosis by analyzing the received user input and localized and seasonal data available to the digital health application 105 (including, by way of example and without limitation, publicly available resources, such as Center for Disease Control (CDC) Flu Activity & Surveillance data). The digital health application 105 may determine the diagnosis by analyzing user input received from a plurality of users, including initial complaints received from a plurality of users (e.g., search history), and by analyzing diagnoses generated for a plurality of users; therefore, the digital health application 105 may determine a diagnosis based upon the received user input and upon medical histories of at least one user having at least one characteristic in common with the user.

In addition to, or instead of, the predictive models described above, the digital health application 105 may determine the diagnosis by applying, to received user input and retrieved data associated with the user, a hybrid model combining recurrent neural network architectures (such as, without limitation, a long short-term memory network (LSTM) and a linear model to determine a level of probability of the diagnosis. The model may access a number of features including information from a patient's clinical history and demographic profile and the received responses to the questions. In embodiments in which the model combines a linear model and an LSTM, the linear model may receive input relating to chronic conditions and allergies while the LSTM may receive input relating to elements that have time components (e.g., most recent clinically assessed urinary tract infection). By way of example, if a patient history indicates the patient has diabetes, the model receives a fixed score as input (which will not vary as diabetes is chronic and binary), while input representing a urinary tract infection may be weighted (or excluded) based on how recent it was clinically assessed.

The digital health application 105 may identify a plurality of possible diagnoses. The digital health application 105 may associate with each of the plurality of possible diagnoses a probability of the diagnosis being accurate. The digital health application 105 may rank the plurality of possible diagnoses by probability (e.g., in order of increasing or decreasing likelihood that a particular diagnosis is accurate). The digital health application 105 may determine to display each of the identified plurality of possible diagnoses in a user interface to the user. The digital health application 105 may determine to display a subset of the identified plurality of possible diagnoses in a user interface to the user. For example, the digital health application 105 may apply a filter to the probabilities associated with each of the possible diagnoses and determine to display any of the possible diagnoses that have a probability of being accurate that exceeds a threshold level of likelihood of accuracy. As another example, the digital health application 105 may determine identify the diagnosis in the plurality of possible diagnoses having the highest probability of being accurate and select that identified diagnosis as the single determined diagnosis that the digital health application 105 will display in the user interface. The digital health application 105 may determine how many of the possible diagnoses to display based on a variety of factors—by way of example, and without limitation, an administrator may specify for a particular medical provider whether the digital health application 105 may display only one or a plurality of possible diagnoses; the digital health application 105 may be configured to only return the most accurate diagnosis; the digital health application 105 may be configured to return all possible diagnoses; the digital health application 105 may be configured to return all possible diagnoses that exceed a threshold level of accuracy; the digital health application 105 may be configured to determine what subset of possible diagnoses to return based on a category of diagnoses (e.g., based on symptoms or severity of illness or other categorization)

The method 200 includes modifying, by the digital health application, a user interface of the digital health application to display an identification of the determined diagnosis (212). The digital health application 105 may select text to display in the user interface after accessing a mapping between text for display and the representation of the diagnosis determined by the digital health application 105. The digital health application 105 may apply a model to determine the diagnosis, as described above, and the model may assign a level of probability of accuracy a unique code corresponding to a particular diagnosis; for at least one diagnosis, the digital health application 105 determines to display the identification of the determined diagnosis, and accesses a table mapping stored in a database (e.g., in the database 103) to retrieve a human-readable description of the determined diagnosis that is mapped to the unique code.

The method 200 includes requesting, by the digital health application, an indication of whether the user of the digital health application accepts the determined diagnosis (214). By way of example, the digital health application 105 may include a first user interface element asking the user to select a second user interface element if the user accepts the diagnosis. Should the user decide that they do not accept the diagnosis and wish to discuss symptoms and the diagnosis with a medical professional, the digital health application 105 may provide functionality for consulting with a health care provider. By way of example, the digital health application 105 may communicate with the provider digital health application 107 regarding the determined diagnosis and underlying user data.

The method 200 includes requesting, by the digital health application, an indication of whether to establish, for the user of the digital health application, a consultation with a medical professional to discuss the determined diagnosis (216). In one embodiment, the user accepted the diagnosis but has questions about the implications of the diagnosis, the course of treatment, or other aspects of the diagnosis and wishes to discuss those questions with the medical professional. In another embodiment, the user denies the diagnosis and wishes to have the determined diagnosis evaluated by a human medical professional. The digital health application 105 may communicate with the provider digital health application 107 regarding the determined diagnosis and underlying user data if the user indicates that the user requests that a medical professional review the determined diagnoses (instead of, or in addition to, the user requesting a consultation with the medical professional. The digital health application 105 may communicate with the provider digital health application 107 in order to establish a consultation (including, but not limited to, scheduling an in-person appointment or a video conference call between the user and the medical professional). The digital health application 105 may establish a network connection between a computing device of the medical professional and a computing device of the user (e.g., establishing a text-based "chat" session between the two computing devices). Therefore, the digital health application 105 may schedule at least one consultation with a medical professional for the user.

In some embodiments, after a consultation between a medical professional and the user, or after a review of the data received by the digital health application 105 and of the determined diagnosis, the digital health application 105 receives, from the medical professional, (e.g., from the provider digital health application 107), an indication that the medical professional has modified the determined diagnosis (e.g., confirming a part of the diagnosis, confirming the diagnosis but modifying a recommended medical order, or indicating that the diagnosis is incorrect). In other embodiments, after a consultation between a medical professional and the user, or after a review of the data received by the digital health application 105 and of the determined diagnosis, the digital health application 105 receives, from the medical professional, an indication that the medical professional has confirmed the determined diagnosis. The digital health application 105 may use this information in determining subsequent diagnoses for subsequent patients; for example, if a patient rejects a diagnosis or wants a medical consultation to get further more information about a diagnosis, the medical professional's subsequent diagnosis, confirming or rejecting the diagnosis of the digital health application 105, will be provided to the model used by the digital health application 105 to determine the diagnoses, which may result in continual improvements to the accuracy of the algorithms executed by the digital health application 105. Therefore, the digital health application 105 may store an indication of a diagnosis and whether the diagnosis was confirmed, modified in part, or rejected entirely, and access such indications in generating a subsequent diagnosis for the same or a different patient.

The digital health application 105 may identify at least one medical order associated with the determined diagnosis, based upon a determination that the user accepted the determined diagnosis. The digital health application 105 may transmit the at least one medical order based upon a determination that the user accepted the determined diagnosis. As will be understood by those of ordinary skill in the art, medical orders may include, without limitation, referrals, prescriptions, lab tests, and so on.

The digital health application 105 may identify one or more actions to take based upon a diagnosis made. The digital health application 105 may identify a reminder message to transmit to the user (e.g., a reminder of an appointment, a reminder to take a medicine, or other reminder). The digital health application 105 may identify treatment options to display to the user. The digital health application 105 may identify interventions to apply under a physician's supervision. The digital health application 105 may identify a care plan for the patient; a care plan may include a best-in-class order set, including patient instructions and follow-ups, that represents the highest level of clinical and evidence-based medicine and allows automated systems to suggest and/or experienced providers to rapidly send care plans tailored to distinct patient groups with minimal modification for a given diagnosis or symptom.

As an example, in an embodiment in which the digital health application 105 diagnoses a patient with an uncomplicated urinary tract infection (UTI), the digital health application 105 may ask the patient at least one safety-related question. Continuing with this example, the digital health application 105 may present a question to the user asking the user to indicate whether or not the user is pregnant and, if the user indicates the user is not pregnant, then the digital health application 105 may generate an antibiotic prescription for the user as part of the user care plan; if the patient is pregnant, then the digital health application 105 may transmit the diagnosis and a suggested care plan to a medical provider.

As an example of providing a follow-up and reminder, the digital health application 105 may determine to generate an automatic follow-up event within a period of time (e.g., six days) to collect feedback from the patient and generate an automatic lab order for a post-treatment urine culture test. Continuing with this example, if the digital health application 105 determines that after the period of time has lapsed, the system 100 has not received any lab order generation, the digital health application 105 may generate a reminder notification to remind the user of the need for the culture test. Continuing with this example, if the result of the culture test is negative and patient has positive feedback, then the clinical case is closed; if the results are positive and/or patient reports persistent symptoms in the feedback, then a clinician will review and ask additional questions and may order additional diagnostic testing/workup to determine diagnosis.

As another example of providing a follow-up and reminder, if the digital health application 105 diagnosed a patient with acute pyelonephritis (kidney infection), the digital health application 105 may determine to transmit the diagnosis to a clinician for further review, editing, and/or approval of a care plan that includes a prescription for antibiotics and urine testing. Continuing with this example, the digital health application 105 may auto-generate a check-in message for the patient in a first period of time (e.g., a number of days) to assess whether the patient has improved and, if so, then the digital health application 105 may auto-generate a second check-in message for the patient in a second period of time (e.g., a number of days greater than the initial number of days) to assure resolution; if the patient has not improved after the first period of time, the digital health application 105 may transmit an instruction to the medical provider to re-review the case, allowing the medical provider to ask additional questions and order additional diagnostic testing.

In some embodiments, the digital health application 105 transmits at least one medical order based upon a determination that the user accepted the determined diagnosis. For example, the digital health application 105 may transmit the at least one medical order to a pharmacy. As another example, the digital health application 105 may transmit the at least one medical order to a hospital. As another example, the digital health application 105 may transmit the at least one medical order to a medical professional.

The digital health application 105 may display at least one suggested action to take, based upon a determination that the user accepted the determined diagnosis. Examples of suggested actions may include following up in a particular period, non-prescription treatments, and lifestyle modifications.

The digital health application 105 may initiate a consultation with a medical professional for the user; for example, and without limitation, by transmitting data regarding the consultation (including data associated with the user and the determined diagnosis) to the provider digital health application 107 of the medical professional). For example, if the user does not accept the diagnosis and wishes to consult with the medical professional, the digital health application 105 may transmit the user's medical record to a medical professional. As another example, if data in the user's medical history suggests that in addition to taking the recommendation actions or following recommended medical orders, the digital health application 105 may determine that the user should speak with the medical professional and initiate a consultation. The digital health application 105 may generate the consultation itself. The digital health application 105 may transmit information regarding the consultation to a scheduling system of the medical professional. In some embodiments, the digital health application 105 may initiate a consultation process at any point during execution of the methods described herein (e.g., after receiving user input to a question, upon attempting but not succeeding at reaching a diagnosis, or at any other time).

Figure 1E:
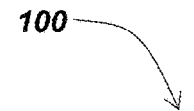
FIG. 1E is a screen shot depicting one embodiment of a set of questions presented to a user.

In some embodiments, the digital health application 105 determines a level of accuracy of the diagnosis. The digital health application 105 may use feedback from the patient to improve subsequent calculations of levels of accuracy. Referring now to FIG. 1E, a screen shot depicts one embodiment of a set of questions presented to a user. As shown in FIG. 1E, the digital health application 105 may automatically generate follow-up questions and present those questions to the user; the system 100 may include functionality for receiving the user input responding to the follow-up questions, analyzing the answers, and evaluating the accuracy of the diagnosis.

Referring now to FIG. 3, a block diagram depicts an embodiment of a system for generating a diagnosis via a digital health application. As shown in FIG. 3, in some embodiments, the digital health application 105 executes on a device (such as a patient mobile device) and interacts directly with one or more databases 103 and also interacts directly with the computing device 106 (including with the provider digital health application 107).

Therefore, in some embodiments, implementation of the methods and systems described herein may provide improved efficiency during the patient interactions, higher quality of diagnoses, improved patient experiences, and result in cost savings to users.

It should be understood that the systems described above may provide multiple ones of any or each of those components and these components may be provided on either a standalone machine or, in some embodiments, on multiple machines in a distributed system. The phrases 'in one embodiment,' 'in another embodiment,' and the like, generally mean that the particular feature, structure, step, or characteristic following the phrase is included in at least one embodiment of the present disclosure and may be included in more than one embodiment of the present disclosure, possibly in combination with other embodiments of the present disclosure. Such phrases may, but do not necessarily, refer to the same embodiment.

The systems and methods described above may be implemented as a method, apparatus, or article of manufacture using programming and/or engineering techniques to produce software, firmware, hardware, or any combination thereof. The techniques described above may be implemented in one or more computer programs executing on a programmable computer including a processor, a storage medium readable by the processor (including, for example, volatile and non-volatile memory and/or storage elements), at least one input device, and at least one output device. Program code may be applied to input entered using the input device to perform the functions described and to generate output. The output may be provided to one or more output devices.

Each computer program within the scope of the claims below may be implemented in any programming language, such as assembly language, machine language, a high-level procedural programming language, or an object-oriented programming language. The programming language may, for example, be LISP, Javascript, Kotlin, Swift, Ruby, PYTHON, PROLOG, PERL, C, C++, C#, JAVA, or any compiled or interpreted programming language.

Each such computer program may be implemented in a computer program product tangibly embodied in a machine-readable storage device for execution by a computer processor. Method steps of the invention may be performed by a computer processor executing a program tangibly embodied on a computer-readable medium to perform functions of the invention by operating on input and generating output. Suitable processors include, by way of example, both general and special purpose microprocessors. Generally, the processor receives instructions and data from a read-only memory and/or a random access memory. Storage devices suitable for tangibly embodying computer program instructions include, for example, all forms of computer-readable devices, firmware, programmable logic, hardware (e.g., integrated circuit chip; electronic devices; a computer-readable non-volatile storage unit; non-volatile memory, such as semiconductor memory devices, including EPROM, EEPROM, and flash memory devices; magnetic disks such as internal hard disks and removable disks; magneto-optical disks; and CD-ROMs). Any of the foregoing may be supplemented by, or incorporated in, specially-designed ASICs (application-specific integrated circuits) or FPGAs (Field-Programmable Gate Arrays). A computer can generally also receive programs and data from a storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium. A computer may also receive programs and data (including, for example, instructions for storage on non-transitory computer-readable media) from a second computer providing access to the programs via a network transmission line, wireless transmission media, signals propagating through space, radio waves, infrared signals, etc.

Figure 4A:
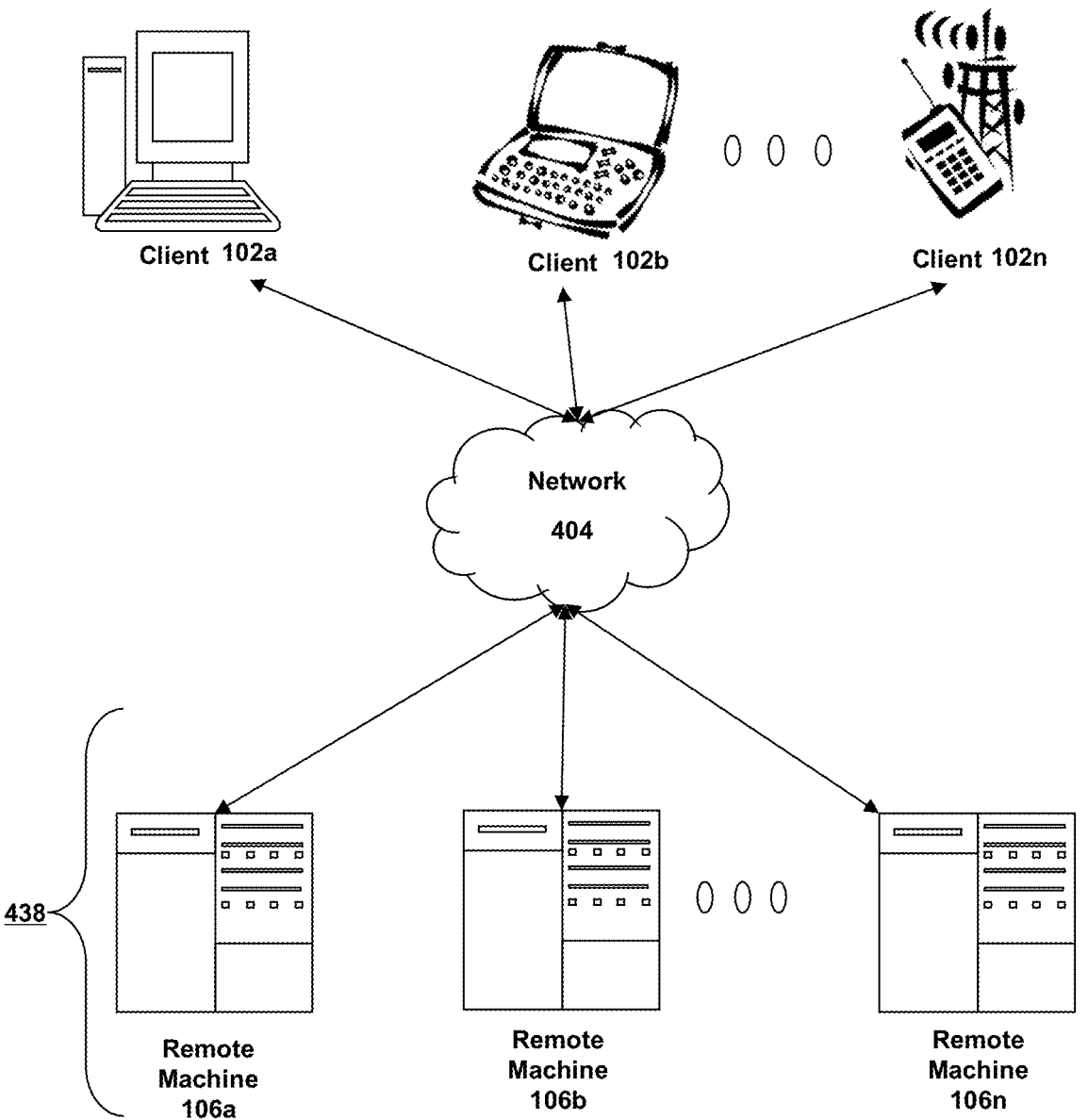
FIGS. 4A, 4B, and 4C are block diagrams depicting embodiments of computers useful in connection with the methods and systems described herein.
Figure 4B:
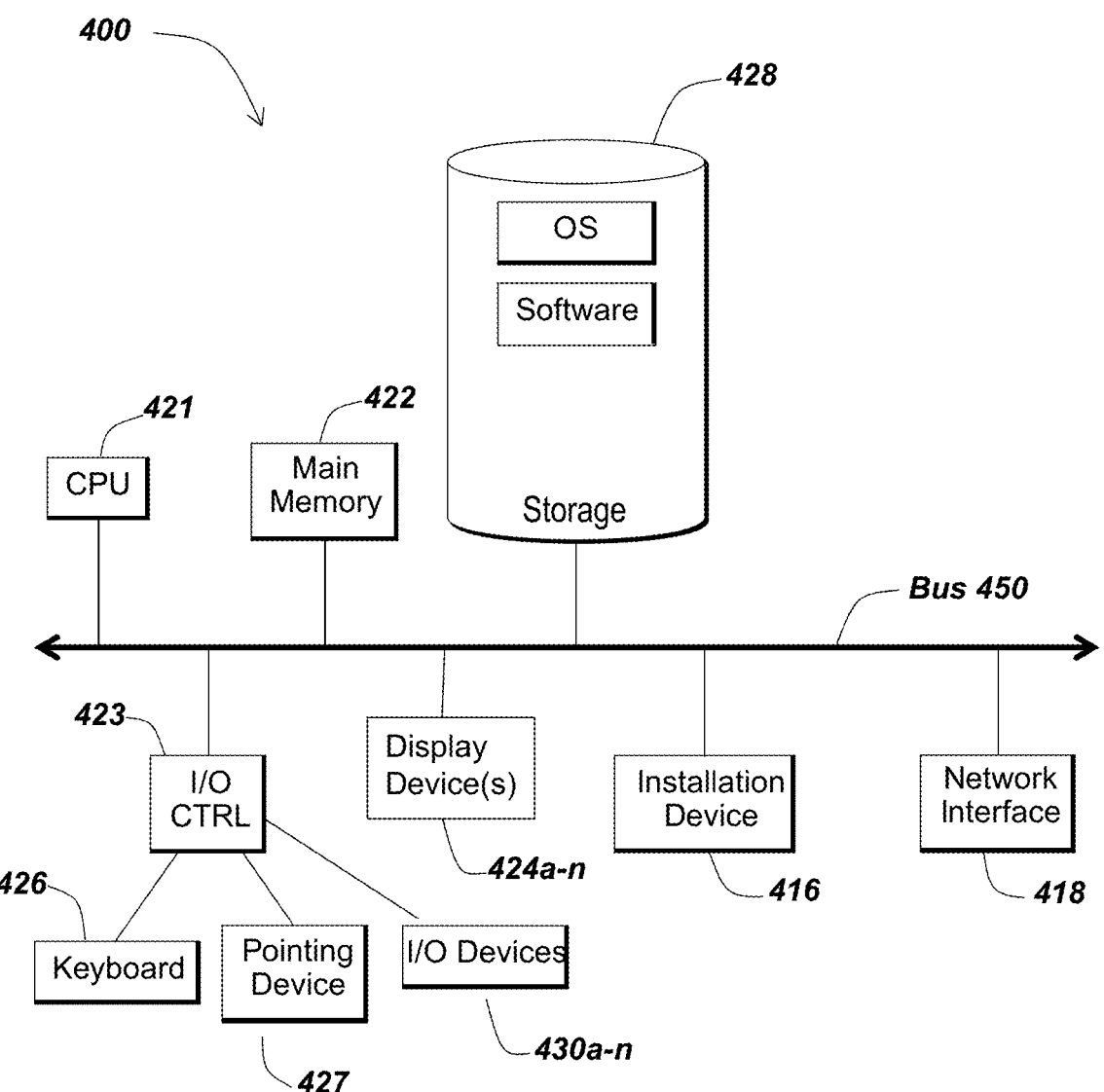
Figure 4C:
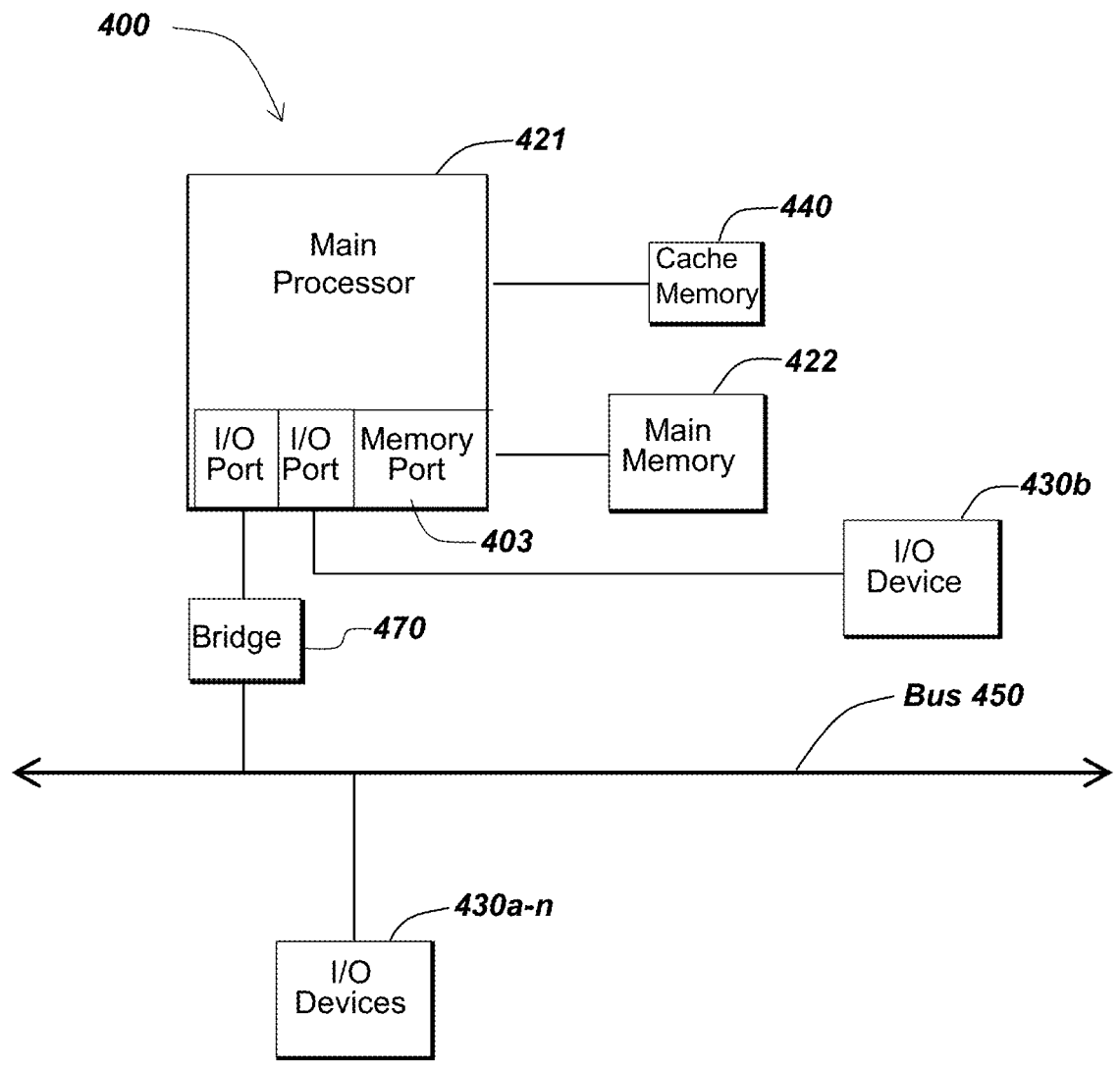

Referring now to FIGS. 4A, 4B, and 4C, block diagrams depict additional detail regarding computing devices that may be modified to execution functionality for implementing the methods and systems described above.

Referring now to FIG. 4A, an embodiment of a network environment is depicted. In brief overview, the network environment comprises one or more clients 102a-102n (also generally referred to as local machine(s) 102, client(s) 102, client node(s) 102, client machine(s) 102, client computer(s) 102, client device(s) 102, computing device(s)102, endpoint(s)102, or endpoint node(s)102) in communication with one or more remote machines 106a-106n (also generally referred to as server(s) 106 or computing device(s) 106) via one or more networks 404.

Although FIG. 4A shows a network 404 between the client(s) 102 and the remote machines 106, the client(s) 102 and the remote machines 106 may be on the same network 404. The network 404 can be a local area network (LAN), such as a company Intranet, a metropolitan area network (MAN), or a wide area network (WAN), such as the Internet or the World Wide Web. In some embodiments, there are multiple networks 404 between the client(s) and the remote machines 106. In one of these embodiments, a network 404' (not shown) may be a private network and a network 404 may be a public network. In another of these embodiments, a network 404 may be a private network and a network 404' a public network. In still another embodiment, networks 404 and 404' may both be private networks. In yet another embodiment, networks 404 and 404' may both be public networks.

The network 404 may be any type and/or form of network and may include any of the following: a point to point network, a broadcast network, a wide area network, a local area network, a telecommunications network, a data communication network, a computer network, an ATM (Asynchronous Transfer Mode) network, a SONET (Synchronous Optical Network) network, an SDH (Synchronous Digital Hierarchy) network, a wireless network, and a wireline network. In some embodiments, the network 404 may comprise a wireless link, such as an infrared channel or satellite band. The topology of the network 404 may be a bus, star, or ring network topology. The network 404 may be of any such network topology as known to those ordinarily skilled in the art capable of supporting the operations described herein. The network 404 may comprise mobile telephone networks utilizing any protocol or protocols used to communicate among mobile devices (including tables and handheld devices generally), including AMPS, TDMA, CDMA, GSM, GPRS, UMTS, or LTE. In some embodiments, different types of data may be transmitted via different protocols. In other embodiments, the same types of data may be transmitted via different protocols.

A client(s) 102 and a remote machine 106 (referred to generally as computing devices 100) can be any workstation, desktop computer, laptop or notebook computer, server, portable computer, mobile telephone, mobile smartphone, or other portable telecommunication device, media playing device, a gaming system, mobile computing device, or any other type and/or form of computing, telecommunications or media device that is capable of communicating on any type and form of network and that has sufficient processor power and memory capacity to perform the operations described herein. A client(s) 102 may execute, operate or otherwise provide an application, which can be any type and/or form of software, program, or executable instructions, including, without limitation, any type and/or form of web browser, web-based client, client-server application, an ActiveX control, or a JAVA applet, or any other type and/or form of executable instructions capable of executing on client(s) 102.

In one embodiment, a computing device 106 provides functionality of a web server. In some embodiments, a web server 106 comprises an open-source web server, such as the NGINX web servers provided by NGINX, Inc., of San Francisco, CA, or the APACHE servers maintained by the Apache Software Foundation of Delaware. In other embodiments, the web server executes proprietary software, such as the INTERNET INFORMATION SERVICES products provided by Microsoft Corporation of Redmond, WA, the ORACLE IPLANET web server products provided by Oracle Corporation of Redwood Shores, CA, or the BEA WEBLOGIC products provided by BEA Systems of Santa Clara, CA.

In some embodiments, the system may include multiple, logically-grouped remote machines 106. In one of these embodiments, the logical group of remote machines may be referred to as a server farm 438. In another of these embodiments, the server farm 438 may be administered as a single entity.

FIGS. 4B and 4C depict block diagrams of a computing device 400 useful for practicing an embodiment of the client(s) 102 or a remote machine 106. As shown in FIGS. 4B and 4C, each computing device 400 includes a central processing unit 421, and a main memory unit 422. As shown in FIG. 4B, a computing device 400 may include a storage device 428, an installation device 416, a network interface 418, an I/O controller 423, display devices 424a-n, a keyboard 426, a pointing device 427, such as a mouse, and one or more other I/O devices 430a-n. The storage device 428 may include, without limitation, an operating system and software. As shown in FIG. 4C, each computing device 400 may also include additional optional elements, such as a memory port 403, a bridge 470, one or more input/output devices 43a-n (generally referred to using reference numeral 430), and a cache memory 440 in communication with the central processing unit 421.

The central processing unit 421 is any logic circuitry that responds to and processes instructions fetched from the main memory unit 422. In many embodiments, the central processing unit 421 is provided by a microprocessor unit, such as: those manufactured by Intel Corporation of Mountain View, CA; those manufactured by Motorola Corporation of Schaumburg, IL; those manufactured by Transmeta Corporation of Santa Clara, CA; those manufactured by International Business Machines of White Plains, NY; or those manufactured by Advanced Micro Devices of Sunnyvale, CA. Other examples include SPARC processors, ARM processors, processors used to build UNIX/LINUX "white" boxes, and processors for mobile devices. The computing device 400 may be based on any of these processors, or any other processor capable of operating as described herein.

Main memory unit 422 may be one or more memory chips capable of storing data and allowing any storage location to be directly accessed by the microprocessor 421. The main memory 422 may be based on any available memory chips capable of operating as described herein. In the embodiment shown in FIG. 4B, the processor 421 communicates with main memory 422 via a system bus 450. FIG. 4C depicts an embodiment of a computing device 400 in which the processor communicates directly with main memory 422 via a memory port 403. FIG. 4C also depicts an embodiment in which the main processor 321 communicates directly with cache memory 440 via a secondary bus, sometimes referred to as a backside bus. In other embodiments, the main processor 421 communicates with cache memory 440 using the system bus 450.

In the embodiment shown in FIG. 4B, the processor 421 communicates with various I/O devices 430 via a local system bus 450. Various buses may be used to connect the central processing unit 421 to any of the I/O devices 430, including a VESA VL bus, an ISA bus, an EISA bus, a MicroChannel Architecture (MCA) bus, a PCI bus, a PCI-X bus, a PCI-Express bus, or a NuBus. For embodiments in which the I/O device is a video display 424, the processor 421 may use an Advanced Graphics Port (AGP) to communicate with the display 424. FIG. 4C depicts an embodiment of a computer 400 in which the main processor 421 also communicates directly with an I/O device 430b via, for example, HYPERTRANSPORT, RAPIDIO, or INFINI-BAND communications technology.

One or more of a wide variety of I/O devices 430a-n may be present in or connected to the computing device 400, each of which may be of the same or different type and/or form. Input devices include keyboards, mice, trackpads, trackballs, microphones, scanners, cameras, and drawing tablets. Output devices include video displays, speakers, inkjet printers, laser printers, 3D printers, and dye-sublimation printers. The I/O devices may be controlled by an I/O controller 423 as shown in FIG. 4B. Furthermore, an I/O device may also provide storage and/or an installation medium 416 for the computing device 400. In some embodiments, the computing device 400 may provide USB connections (not shown) to receive handheld USB storage devices such as the USB Flash Drive line of devices manufactured by Twintech Industry, Inc. of Los Alamitos, CA.

Referring still to FIG. 4B, the computing device 400 may support any suitable installation device 416, such as a floppy disk drive for receiving floppy disks such as 3.5-inch, 5.25-inch disks or ZIP disks; a CD-ROM drive; a CD-R/RW drive; a DVD-ROM drive; tape drives of various formats; a USB device; a hard-drive or any other device suitable for installing software and programs. In some embodiments, the computing device 400 may provide functionality for installing software over a network 404. The computing device 400 may further comprise a storage device, such as one or more hard disk drives or redundant arrays of independent disks, for storing an operating system and other software. Alternatively, the computing device 400 may rely on memory chips for storage instead of hard disks.

Furthermore, the computing device 400 may include a network interface 418 to interface to the network 404 through a variety of connections including, but not limited to, standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or some combination of any or all of the above. Connections can be established using a variety of communication protocols (e.g., TCP/IP, IPX, SPX, NetBIOS, Ethernet, ARCNET, SONET, SDH, Fiber Distributed Data Interface (FDDI), RS232, IEEE 802.11, IEEE 802.11a, IEEE 802.11b, IEEE 802.11g, IEEE 802.11n, 802.15.4, Bluetooth, ZIGBEE, CDMA, GSM, WiMax, and direct asynchronous connections). In one embodiment, the computing device 400 communicates with other computing devices 100' via any type and/or form of gateway or tunneling protocol such as Secure Socket Layer (SSL) or Transport Layer Security (TLS). The network interface 418 may comprise a built-in network adapter, network interface card, PCMCIA network card, card bus network adapter, wireless network adapter, USB network adapter, modem, or any other device suitable for interfacing the computing device 400 to any type of network capable of communication and performing the operations described herein.

In further embodiments, an I/O device 430 may be a bridge between the system bus 150 and an external communication bus, such as a USB bus, an Apple Desktop Bus, an RS-232 serial connection, a SCSI bus, a FireWire bus, a FireWire 800 bus, an Ethernet bus, an AppleTalk bus, a Gigabit Ethernet bus, an Asynchronous Transfer Mode bus, a HIPPI bus, a Super HIPPI bus, a SerialPlus bus, a SCI/LAMP bus, a FibreChannel bus, or a Serial Attached small computer system interface bus.

A computing device 400 of the sort depicted in FIGS. 4B and 4C typically operates under the control of operating systems, which control scheduling of tasks and access to system resources. The computing device 400 can be running any operating system such as any of the versions of the MICROSOFT WINDOWS operating systems, the different releases of the UNIX and LINUX operating systems, any version of the MAC OS for Macintosh computers, any embedded operating system, any real-time operating system, any open source operating system, any proprietary operating system, any operating systems for mobile computing devices, or any other operating system capable of running on the computing device and performing the operations described herein. Typical operating systems include, but are not limited to: WINDOWS 3.x, WINDOWS 95, WINDOWS 98, WINDOWS 2000, WINDOWS NT 3.1-4.0, WINDOWS CE, WINDOWS XP, WINDOWS 7, WINDOWS 8, WINDOWS VISTA, and WINDOWS 10, all of which are manufactured by Microsoft Corporation of Redmond, WA; any version of MAC OS manufactured by Apple Inc. of Cupertino, CA; OS/2 manufactured by International Business Machines of Armonk, NY; Red Hat Enterprise Linux, a Linus-variant operating system distributed by Red Hat, Inc., of Raleigh, NC; Ubuntu, a freely-available operating system distributed by Canonical Ltd. of London, England; or any type and/or form of a Unix operating system, among others.

The computing device 400 can be any workstation, desktop computer, laptop or notebook computer, server, portable computer, mobile telephone or other portable telecommunication device, media playing device, a gaming system, mobile computing device, or any other type and/or form of computing, telecommunications or media device that is capable of communication and that has sufficient processor power and memory capacity to perform the operations described herein. In some embodiments, the computing device 400 may have different processors, operating systems, and input devices consistent with the device. In other embodiments, the computing device 400 is a mobile device, such as a JAVA-enabled cellular telephone/smartphone or personal digital assistant (PDA). The computing device 400 may be a mobile device such as those manufactured, by way of example and without limitation, by Apple Inc. of Cupertino, CA; Google/Motorola Div. of Ft. Worth, TX; Kyocera of Kyoto, Japan; Samsung Electronics Co., Ltd. of Seoul, Korea; Nokia of Finland; Hewlett-Packard Development Company, L.P. and/or Palm, Inc. of Sunnyvale, CA; Sony Ericsson Mobile Communications AB of Lund, Sweden; or Research In Motion Limited of Waterloo, Ontario, Canada. In yet other embodiments, the computing device 400 is a smartphone, POCKET PC, POCKET PC PHONE, or other portable mobile device supporting Microsoft Windows Mobile Software.

In some embodiments, the computing device 400 is a digital audio player. In one of these embodiments, the computing device 400 is a digital audio player such as the Apple IPOD, IPOD TOUCH, IPOD NANO, and IPOD SHUFFLE lines of devices manufactured by Apple Inc. In another of these embodiments, the digital audio player may function as both a portable media player and as a mass storage device. In other embodiments, the computing device 400 is a digital audio player such as those manufactured by, for example, and without limitation, Samsung Electronics America of Ridgefield Park, NJ, or Creative Technologies Ltd. of Singapore. In yet other embodiments, the computing device 400 is a portable media player or digital audio player supporting file formats including, but not limited to, MP3, WAV, M4A/AAC, WMA Protected AAC, AEFF, Audible audiobook, Apple Lossless audio file formats, and .mov, . m4v, and .mp4 MPEG-4 (H.264/MPEG-4 AVC) video file formats.

In some embodiments, the computing device 400 comprises a combination of devices, such as a mobile phone combined with a digital audio player or portable media player. In one of these embodiments, the computing device 400 is a device in the Google/Motorola line of combination digital audio players and mobile phones. In another of these embodiments, the computing device 400 is a device in the IPHONE smartphone line of devices manufactured by Apple Inc. In still another of these embodiments, the computing device 400 is a device executing the ANDROID open source mobile phone platform distributed by the Open Handset Alliance; for example, the device 100 may be a device such as those provided by Samsung Electronics of Seoul, Korea, or HTC Headquarters of Taiwan, R.O.C. In other embodiments, the computing device 400 is a tablet device such as, for example and without limitation, the IPAD line of devices manufactured by Apple Inc.; the PLAYBOOK manufactured by Research In Motion; the CRUZ line of devices manufactured by Velocity Micro, Inc. of Richmond, VA; the FOLIO and THRIVE line of devices manufactured by Toshiba America Information Systems, Inc. of Irvine, CA; the GALAXY line of devices manufactured by Samsung; the HP SLATE line of devices manufactured by Hewlett-Packard; and the STREAK line of devices manufactured by Dell, Inc. of Round Rock, TX.

Having described certain embodiments of methods and systems for generating diagnoses via digital health applications, it will now become apparent to one of skill in the art that other embodiments incorporating the concepts of the disclosure may be used. Therefore, the disclosure should not be limited to certain embodiments, but rather should be limited only by the spirit and scope of the following claims.

What is claimed is:

1. A method for generating a diagnosis via a digital health application in a virtual primary care practice, the method comprising:

receiving, by a digital health application executing on a computing device and executing in a patient-facing mode, via a user interface of the digital health application, from a patient, a request for a diagnosis including an initial complaint, wherein receiving further comprises identifying, by the digital health application, a key word in the initial complaint and performing a key word search of a database using the key word to identify at least one plurality of questions;

selecting, by the digital health application, the identified plurality of questions from the database based on the initial complaint and an order of presenting each of the plurality of questions, the order associated with the plurality of questions;

displaying, by the digital health application, to the patient using the digital health application, in the associated order, each of the plurality of questions;

receiving, by the digital health application, user input responsive to each of the plurality of questions;

determining, by the digital health application, a diagnosis based upon the received user input, wherein determining further comprises using natural language processing on patient data and applying a neural network model to determine the diagnosis and a level of probability of the determined diagnosis;

modifying, by the digital health application, the user interface of the digital health application to display an identification of the determined diagnosis;

requesting, by the digital health application, a selection, by the patient using the digital health application, of a user interface element in the user interface indicating whether or not the patient accepts the determined diagnosis; and requesting, by the digital health application, subsequent to receiving, by the digital health application, a selection of the user interface element indicating that the patient does not accept the determined diagnosis, an indication of whether to establish, for the patient using the digital health application, a consultation with a medical professional to discuss the determined diagnosis.

2. The method of claim 1 further comprising initiating, by the digital health application, a sequence of questions from the plurality of questions.

3. The method of claim 1, wherein receiving, by the digital health application, user input further comprises receiving a photograph.

4. The method of claim 1, wherein receiving, by the digital health application, user input further comprises receiving a text-based response via a user interface.

5. The method of claim 1 further comprising:

after receiving user input responsive to a first of the plurality of questions, modifying, by the digital health application, the associated order;

selecting, by the digital health application, a second of the plurality of questions according to the modified order; and displaying, by the digital health application, the second of the plurality of questions.

6. The method of claim 1 wherein determining the diagnosis further comprises applying, by the digital health application, a hybrid model combining a long short-term model and a linear model to determine a level of probability of the diagnosis.

7. The method of claim 1 wherein determining the diagnosis further comprises applying, by the digital health application, a linear model to determine a level of probability of the diagnosis.

8. The method of claim 1 wherein determining the diagnosis further comprises determining, by the digital health application, a diagnosis based upon the received user input and upon longitudinal data associated with the patient.

9. The method of claim 1 wherein determining the diagnosis further comprises determining, by the digital health application, a diagnosis based upon the received user input and upon a medical history associated with the patient.

10. The method of claim 1 wherein determining the diagnosis further comprises determining, by the digital health application, a diagnosis based upon the received user input and upon medical histories of at least one user having at least one characteristic in common with the patient.

11. The method of claim 1 wherein determining the diagnosis further comprises determining, by the digital health application, a diagnosis based upon the received user input and upon localized and seasonal data available to the digital health application.

12. The method of claim 1 further comprising receiving, by the digital health application, from the medical professional, an indication that the medical professional has confirmed the determined diagnosis.

13. The method of claim 1 further comprising receiving, by the digital health application, from the medical professional an indication that the medical professional has modified the determined diagnosis.

14. The method of claim 1 further comprising identifying, by the digital health application, at least one medical order associated with the determined diagnosis, based upon a determination that the patient accepted the determined diagnosis.

15. The method of claim 1 further comprising transmitting, by the digital health application, at least one medical order based upon a determination that the patient accepted the determined diagnosis.

16. The method of claim 1 further comprising displaying, by the digital health application, at least one suggested action to take, based upon a determination that the patient accepted the determined diagnosis.

17. The method of claim 1 further comprising scheduling, by the digital health application, at least one consultation with a medical professional for the patient.

18. The method of claim 1 further comprising establishing, by the digital health application, a network connection between a medical professional and the patient.

19. A non-transitory, computer readable medium comprising computer program instructions tangibly stored on the computer readable medium, wherein the computer program instructions are executable by at least one computer processor to perform a method for generating a diagnosis via a digital health application in a virtual primary care practice, the method comprising:

receiving, by a digital health application executing on a computing device and executing in a patient-facing mode, via a user interface of the digital health application from a patient, a request for a diagnosis including an initial complaint, wherein receiving further comprises identifying, by the digital health application, a key word in the initial complaint and performing a key word search of a database using the key word to identify at least one plurality of questions;

selecting, by the digital health application, a plurality of questions from the database based on the initial complaint and an order of presenting each of the plurality of questions, the order associated with the plurality of questions;

displaying, by the digital health application, to the patient using the digital health application, in the associated order, each of the plurality of questions;

receiving, by the digital health application, user input responsive to each of the plurality of questions;

determining, by the digital health application, a diagnosis based upon the received user input, wherein determining further comprises using natural language processing on patient data and applying a neural network model to determine the diagnosis and a level of probability of the determined diagnosis;

modifying, by the digital health application, the user interface of the digital health application to display an identification of the determined diagnosis;

requesting, by the digital health application, a selection, by the patient using the digital health application, of a user interface element in the user interface indicating whether or not the patient accepts of the determined diagnosis; and requesting, by the digital health application, subsequent to receiving, by the digital health application, a selection of the user interface element indicating that the patient does not accept the determined diagnosis, an indication of whether to establish, for the patient using the digital health application, a consultation with a medical professional to discuss the determined diagnosis.

* * * * *